United States Patent [19]

Heimke et al.

[11] 4,031,571
[45] June 28, 1977

[54] HIP ENDOPROSTHESIS WITH STEPPED LOAD-TRANSFERRING SURFACES

[75] Inventors: Günther Heimke, Mannheim; Peter Griss, Plankstadt, both of Germany

[73] Assignee: Friedrichsfeld GmbH Steinzeug-und Kunststoffwerke, Postfach, Germany

[22] Filed: Dec. 24, 1975

[21] Appl. No.: 644,332

[30] Foreign Application Priority Data
Dec. 24, 1974 Germany .......................... 2461339
Apr. 22, 1975 Germany .......................... 2517702

[52] U.S. Cl. .............................. 3/1.913; 128/92 C; 128/92 CA
[51] Int. Cl.² ......................................... A61F 1/24
[58] Field of Search ........................ 3/1, 1.9–1.913; 128/92 C, 92 CA

[56] References Cited
UNITED STATES PATENTS 3,067,740  12/1962  Haboush .................... 128/92 CA
3,685,058  8/1972   Tronzo ..................... 3/1.912
3,740,769  6/1973   Haboush .................... 3/1.912
3,744,061  7/1973   Frost ...................... 3/1.912

FOREIGN PATENTS OR APPLICATIONS 2,306,552  8/1974   Germany .................... 3/1.91
2,324,865  11/1974  Germany .................... 3/1.913
2,324,867  11/1974  Germany .................... 3/1.9
471,394    5/1952   Italy ...................... 128/92 CA

OTHER PUBLICATIONS

"Richards Bechtol Femoral Prosthesis" (Standard & Long Stem SMO Type 316 Stainless Steel), Richards Manufacturing Company (Brochure Advertisement), Memphis, Tenn., received Aug. 24, 1966.

Primary Examiner—Ronald L. Frinks
Attorney, Agent, or Firm—George H. Mitchell, Jr.

[57] ABSTRACT

The thigh portion of an endoprosthesis for hip joints is provided with stepped projecting surfaces to distribute forces in the bone tissue.

15 Claims, 4 Drawing Figures

HIP ENDOPROSTHESIS WITH STEPPED LOAD-TRANSFERRING SURFACES

This invention relates to the thigh portion of a total endoprosthesis for cement-free implantation in the hip joint in which the head, neck, neck contacting surface and thigh shaft are made of a bio-inert or a bio-active material or some combination of the two so as to be biologically benign. Implants of this type are used as replacements for the hip joint.

It is known to make the femur portion of a total endoprosthesis for cement-free implantation from a material consisting of a compact, dense, aluminum-oxide ceramic, the surface parts of which serve for the anchoring in the thigh bone and may possibly be covered with a layer of a bio-active material for stimulating the growing together of the bone tissue, such a material being disclosed in DT-OS 2,324,867 and U.S. Pat. No. 3,919,713. The implant may also be made of one of the super strong metals, the surfaces of which are likewise covered with a bio-active layer of material for stimulating the growing-on of the tissues, while at the same time separating the metal from the tissue as disclosed in DT-OS 2,306,552. The quick growing-on of the bone tissue on the endoprosthesis is favorable, for one thing, because the patient is expected to become ambulatory as quickly as possible after the operation in order to avoid thrombosis and, for another thing, because the resulting forces can be transferred better into the bone. Thus, the object of the invention is to obtain a firm anchoring of the endoprosthesis in the bone of the hip joint, while taking advantage of natural conditions.

A solution of this problem consists in the fact that according to the invention, all of the load bearing surfaces are disposed perpendicular to the longitudinal orientation of the spicules of the spongy tissues, these surfaces being distributed in the form of steps, the steps on one side of the shaft being designed to transmit the load while another set of steps on the opposite side are designed to transmit pulling forces.

A theoretical form of endoprosthesis has been disclosed in the literature in which the shaft of the femur portion is provided with a "Christmas Tree" form of structure (see J. Charnley "Biochemical Analysis of the Use of Cement to Anchor the Femoral Head Prosthesis", Journal of Bone and Joint Surgery, Vol. 47B, No. 2, May 1965, pp. 354–363). However, this type of prosthesis has been mentioned only in connection with implantation by means of a bone cement and merely to demonstrate the distribution of the various forces.

Furthermore, a metal prosthesis for implantation without cement has also been known which is provided on its inner side with a small sawtooth surface of a similar kind (see Mittelmeier H., "Anchoring Without Cement...", Z. Orthop., 112,27–33; 1974). However, such metal prostheses, as is well known, do not have a bio-inert surface, with the result that there will be adverse reactions with the bone tissue.

These previously known prostheses lack the characteristic, nevertheless, that all of the load transferring surfaces be disposed perpendicularly with respect to the longitudinal orientation of the spongy structures in the surrounding tissue. This perpendicular orientation results in a surprisingly favorable, biomechanical load. Whenever the spicule of the spongy bone structure are considered as a family of curves, then one may speak abstractly as well as mathematically, of the longitudinal orientation of the family of curves.

A further advantage of the invention consists in the fact that the total area of the contacting surface is considerably larger than in the case of the prior known types of prostheses, as a result of which, the pressure at the surfaces becomes correspondingly smaller.

Furthermore, the contact surface of the collar surrounding the neck can be oriented at an angle with respect to the horizontal which is more acute than the value of the natural angle of the neck of the thigh for the angular position of said surface. From the above-mentioned work of Charnley, it is disclosed that the value which results from the natural angle of the femur neck for the angular position of the contact surface is about 45°. Orientation of the contact surface at a more acute angle in accordance with the present invention, results in a larger contact surface around the neck than hitherto and thus opens the possibility of achieving an inner or outer shifting of the neck peg carrying the femur head on the surface parallel to the contact surface of the neck on the collar part. Thus, a biomechanically, more favorable arrangement of the prosthesis is made possible to provide better accomodation to individual circumstances. Naturally, the various types of prosthesis can be put at the disposal of the surgeon.

In contradistinction to the previously mentioned prosthesis having the sawtooth surfaces on the inner surface, in the case of the present invention, load supporting surfaces or steps, are also provided on the outer surface of the prosthesis shaft. In accordance with the theory of the invention, that all surfaces for the transfer of a load should be aligned perpendicularly to the orientation of the spicules of the spongy structure, the surfaces on the outer side of the shaft face in an opposite direction from the surfaces provided on the inner side. In accordance with the findings resulting from animal experiments, it is considered that pressure-absorbing bony structures (resulting from changing loads) are formed on these surfaces. Collagen fibers would accumulate at these bone structures which cause a transformation of forces of compression into forces in tension and the introduction of these forces into the thigh bone from the outer portion of the shaft. This type of introduction of the load from the prosthesis into the bone could be described as "step tensioning" and assures a deflection of forces and direct absorption of the load. The arrangement on the outer surface of the shaft therefore comes very close to the natural biomechanical load configuration and thus makes possible a more durable implantation of the prosthesis.

Furthermore, it is desirable that the load transfer surfaces of the individual steps be aligned at various angles with respect to the horizontal. Preferably, the stepped surfaces are oriented to correspond with the condition of the spongy structure surrounding the shaft after implantation and, as far as possible, it should be designed in accordance with the individual anatomy. The reaction forces of the bone structure, can be found by a series of experiments as, for example, with sheep.

In the case of certain anatomical conditions, such as are frequently met in the case of deformed hip joints, a straight or flat contact surface at the neck of the prosthesis on the thigh bone is not possible. In this case, an angular contact surface at the neck can be provided and, in combination with the previously described stepped surfaces, it will be possible, even in the case of deformed hip joints, to achieve an optimum fit against the orientation of the spongy structure and therefore, a biomechanically favorable transfer of forces between the shaft and the bone.

Preferably, the shaft of the thigh part of the endoprosthesis is disposed asymmetrically with respect to the upper part, or head, of the prosthesis when viewed from the side. This results in a more favorable introduction of force into the hollow portions of the thigh bone as a result of the asymmetry than was possible in the prior prostheses construction and the bending stress on the entire thigh part of the prosthesis is considerably reduced. This is favorable both for the strength and durability of the prosthesis under its changing load, as well as for the biomechanically improved bone reaction to the body of the prosthesis.

In addition, a modified form of the invention has been developed which reduced the possibility of the loosening of the implant over a period of time. In this connection, it should also be noted that the femur parts of a hip joint endoprosthesis have been attached by the use of plastic bone cement introduced into the upper part of the bone marrow space. However, this method of anchoring has certain disadvantages which lie especially in the hardening characteristics of plastic bone cements. These cements, during hardening, attain surface temperatures which are above the albumin coagulation temperature and at the same time, they generate fairly large quantities of monomer during hardening to the surrounding tissue. As a result, the surrounding tissue is damaged, so that in most cases, no intimate contact is established between the bone tissue and the surface of the bone cement which involves a danger of loosening of the implantation. In addition, these plastic bone cements exhibit long-term aging of their mechanical characteristics, the possible result of which is the loosening of the prosthesis.

The endoprostheses used in the past with these bone cements have usually consisted of metal, but these metal implants have also been proposed for anchoring without cement. Ceramic implants, especially those made of dense $Al_2O_3$ material, have also been tested as described in DOS 2,324,865; and U.S. Pat. No. 3,924,275.

Nevertheless, extensive experiments with animals have shown that all of the prior types of implants, whether implanted with the use of a cement or whether implanted without cement, do not provide a completely satisfactory anchoring of the femur part of an endoprosthesis for the hip joint.

On the other hand, it has turned out that, with the use of the stepped load-transferring surfaces on the shaft of a prosthesis, it is possible to succeed in stabilization of the prosthesis at the upper end of the femur to prevent shifting of the prosthesis in a direction parallel to the axis of the shaft. With the use of biomechanically correct supporting surfaces along the shaft of the prosthesis, it is possible to prevent bone-resorption in the corticalis in the area of the prosthesis and thus, guarding against an increased possiblity of fracture or at least reducing the danger.

However, the animal experiments referred to above have also shown that none of the procedures used in the past will guarantee stability against twisting, or rotation, of the femur portion of the prosthesis. Even when the cross-section of the shaft is essentially elongated, such as in the shape of an oval, trapezoidal or rectangular, it has been found again and again that the prosthesis is not firmly anchored against twisting with respect to the longitudinal axis. This has been found to be true, for example, in the case of prostheses implanted in sheep after an experimental period of up to 1 year and wherein the shaft is made of a practically completely bio-inert $Al_2O_3$ ceramic. The cause of this behavior is assumed to be the fact that the femur, at least in this area, is not in a position to form bone structures which can absorb permanently forces which attack in a direction perpendicular to the femur axis on the inside of the corticalis. It has even been observed that apparently completely solidly fixed femur portions of endoprostheses made of $Al_2O_3$ ceramic have, nevertheless, become loosened with respect to rotation about the longitudinal axis.

It has, therefore, become necessary to develop a configuration for the shaft of the prosthesis which will permit implantation without the use of cement and which will also guarantee the necessary stability against rotation with respect to the axis of the femur portion.

It has turned out that the solution to the problem consists in providing the shaft of the prosthesis with elongated indentations on at least two opposite sides, these indentations having boundaries which extend across the width of the shaft along angles which deviate from 90° with respect to the general shaft axis, with the boundaries on one side of the shaft being shifted in the opposite direction from the boundaries on the other side of the shaft.

The two sides which are provided with these indentations can be the front and rear surfaces of the prosthesis shaft in the case of a shaft which is of a generally rectangular cross-section. In this case, the inner and outer surfaces of the shaft can also be advantageously provided with the load-transferring ribs or steps described in connection with the previously described form of the invention. The desirable materials for constructing prostheses according to the invention include many bio-inert, raw materials. A compact, or dense, $Al_2O_3$ ceramic in which more than 96% of the ceramic consists of $Al_2O_3$, has proven to be particularly favorable since, in addition, this $Al_2O_3$ ceramic can advantageously be provided with bio-active surface coatings, which coatings bring about an improvement of the bone formation on the surface of the implantation, such materials being disclosed in DOS 2,324,867 and U.S. Pat. No. 3,919,723.

However, when the shaft of the prosthesis consists of a metal, it will be desirable to provide all of the surfaces which come in contact with the tissue with at least one layer of a dense glass or glass-like coating, such as the glass ceramic disclosed in DOS 2,306,552.

Experiments with animals, such as sheep, have shown that the indentations provided on the shaft of a prosthesis in accordance with this invention, provides just as much insurance against twisting of the shaft as it has been possible to achieve in the past by a special collar on the femur part of the endoprosthesis, especially in connection with the load-transferring steps previously described for the stabilization of movement in directions parallel with the axis. At the same time, it is relatively easy to separate the two functions of stabilization in a direction parallel with the axis and of preventing rotation of the shaft, due to the fact that the steps are provided on the inside and outside surfaces of the shaft while the elongated indentations, designed to prevent twisting, are provided on the front and rear sides. The disposal of the steps in the manner stated provides a particularly favorable transfer of forces parallel to the shaft from the prosthesis into the femur.

The advantages of the shaft configured in accordance with the invention is particularly favorable whenever a bio-inert $Al_2O_3$ ceramic is used for making the shaft since the reaction of the tissue on the surface of the material does not cause any repulsion of the implantation. The development of bone tissue on the surface of the implant is accelerated by the use of bio-active substances which results in a shortening of the time for integration of the prosthesis with the tissue and thus to an earlier development of maximum load-carrying capacity with consequent advantages for the patient. However, whenever the shaft of the prosthesis is made of metal, then a coating of glass ceramic or other inert material results in a similar acceleration of the healing process.

Further objects and advantages will be apparent to those skilled in the art after reading the following description in connection with the attached drawings in which.

Figure 1:
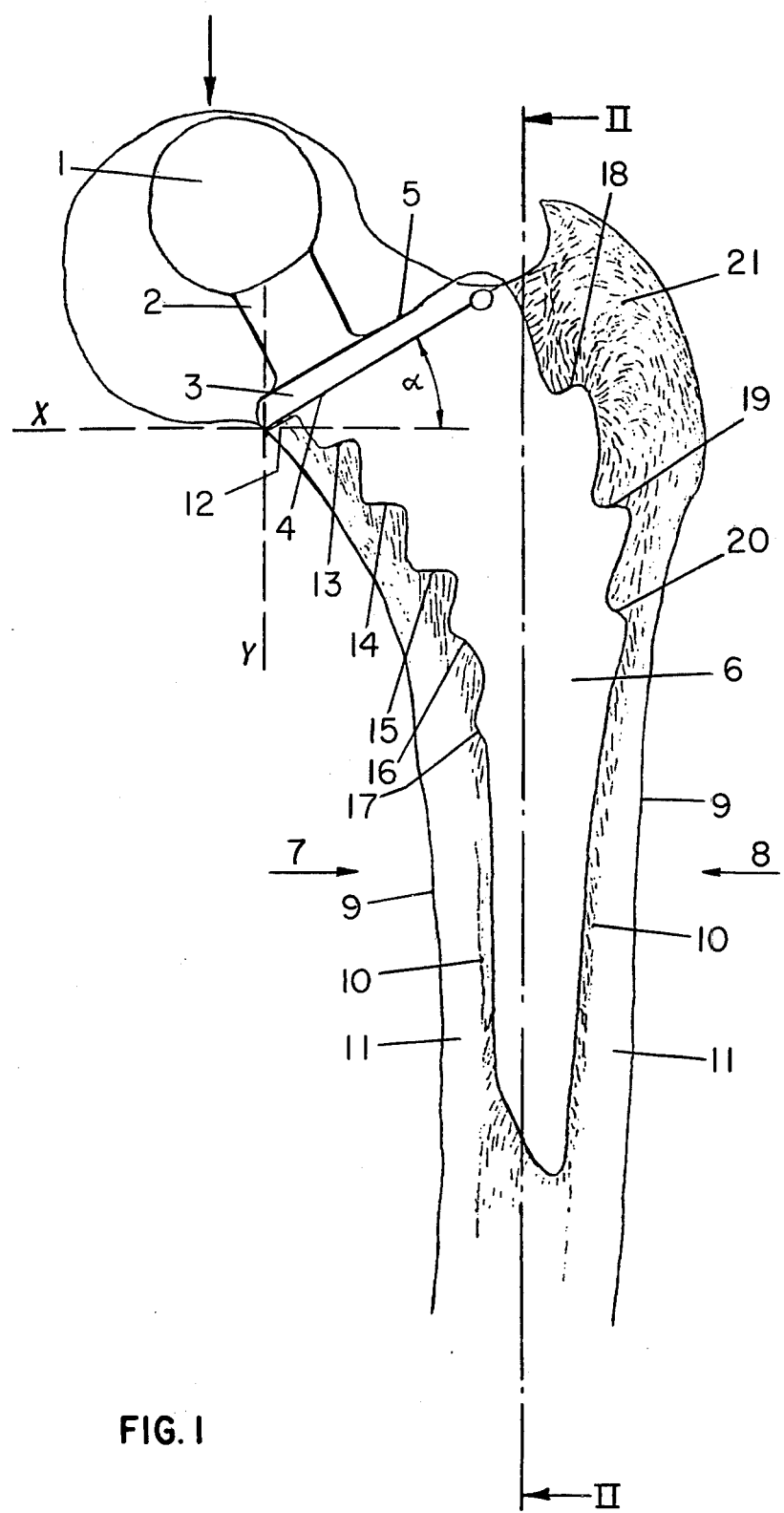
FIG. 1 is a front elevation of a preferred form of the thigh portion of a total endoprosthesis for a hip joint shown as implanted in the thigh bone.

As can be seen from FIG. 1, a preferred form of thigh portion of the endoprosthesis comprises a femur head 1, joined by a neck portion 2 and an outwardly projecting collar 3 having a lower contacting surface 4 and an upper parallel surface 5, to the upper end of a femur shaft 6. For a better understanding of the invention, the use of the terms "inner" and "outer" sides are employed; the inner side of the shaft being the one which is viewed in the direction of the arrow 7, while the outer side of the shaft is that viewed in the direction indicated by the arrow 8. Furthermore, the level of the horizontal plane is indicated by the dotted line X with the plane of the vertical indicated by the dotted line Y. It can thus be seen that the contact surface 4 of the neck forms with the horizontal plane X and angle $\alpha$ which is more acute than the natural angle of the femur neck which is normally exhibited. The value for the angle $\alpha$ can be about 30°.

In FIG. 1, the numeral 9 indicates the thigh bone itself and numeral 10 denotes generally the outer limits of the spongy portion which merges into the dense compact outer portion 11. Within the area indicated by 10 and adjacent to the surfaces of the shaft 6, there can also be seen the elongated spicules of bone as well as the inner surfaces 12, 13, 14, 15, 16 and 17 on the inner side of the shaft which are disposed at right angles to the adjacent spicules in each location of the stepped portions. On the outer side of the shaft, the stepped portions 18, 19 and 20 are shown as facing in an upward direction at various angles which are perpendicular to the adjacent spicules of the spongy material. The number and the particular orientation of all of the load-transferring surfaces from 12 through 20 can be varied according to the circumstances and conditions of the bone in which the shaft is to be implanted.

Figure 2:
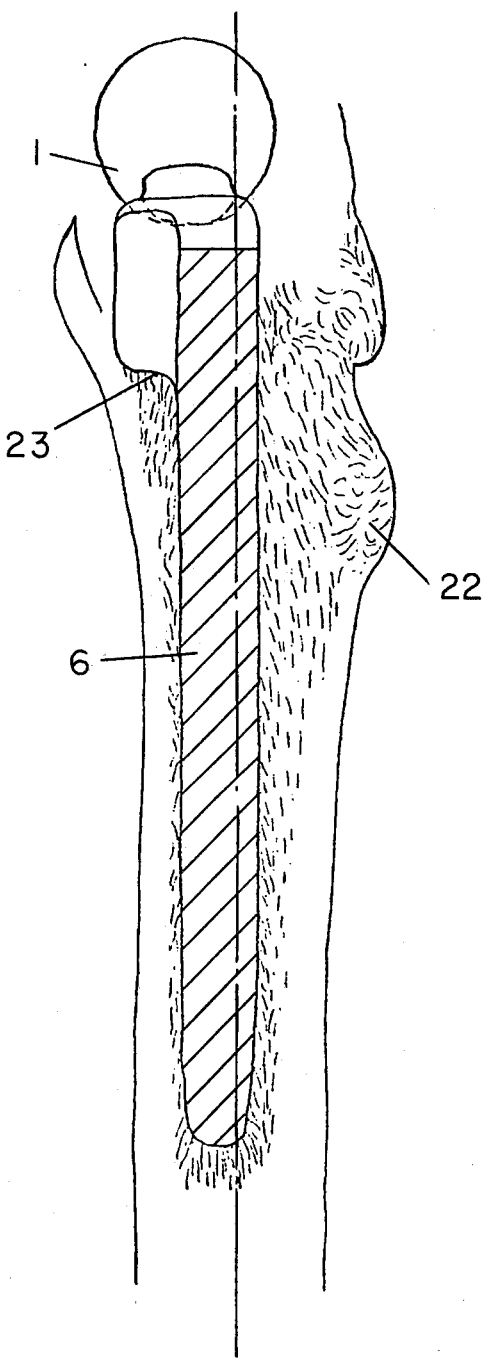
FIG. 2 is a cross-section taken in the line II—II of FIG. 1.

In FIG. 2, it will be observed that the shaft 6 may be arranged asymmetrically with respect to the center line of the upper portion of the prosthesis, this upper portion being provided with a wide load-transferring undersurface 23 while the characteristic "trochanter minor" 22 can be seen.

Figure 3:
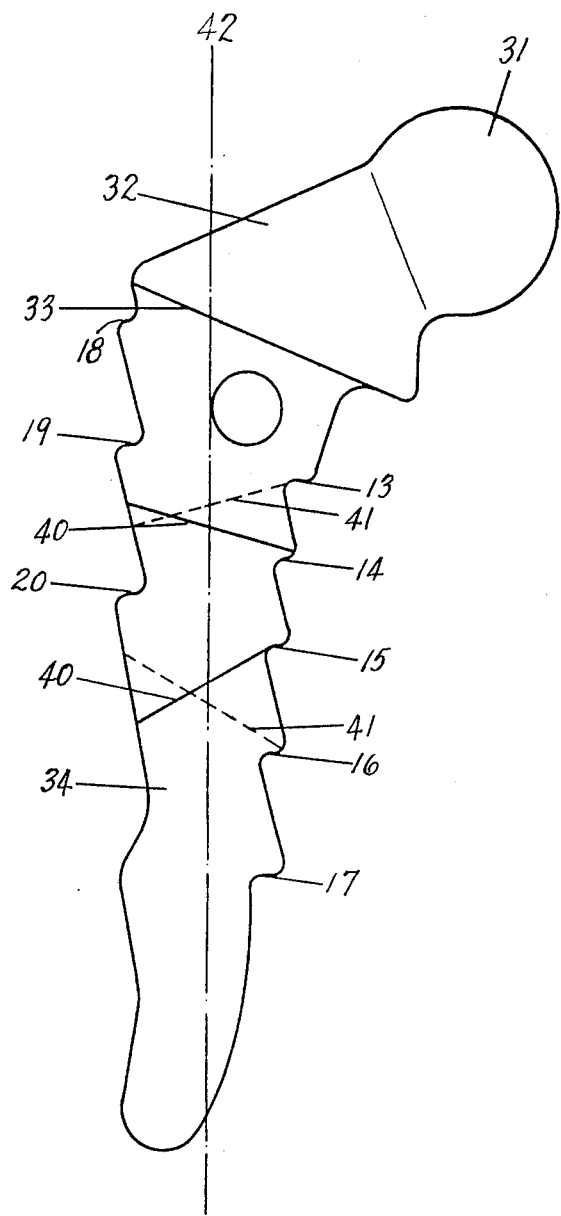
FIG. 3 is a front elevation of a modified form of thigh portion endoprosthesis.
Figure 4:
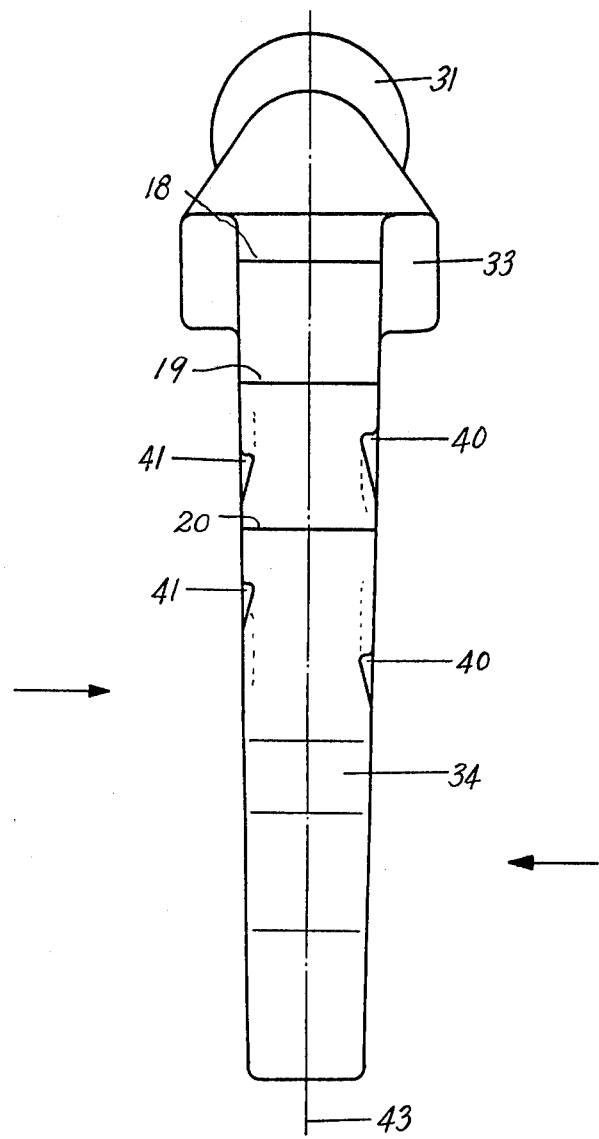
FIG. 4 is a side elevation of the thigh portion shown in FIG. 3 as viewed from the left-hand, or outer, side.

In the second embodiment of the invention, disclosed in FIGS. 3 and 4, the stepped surfaces for transmitting forces in upward and downward directions are indicated, as before, by numerals 13–20, the stepped portions 13–17 being disposed on the inner surface while those indicated by numerals 18, 19 and 20 are disposed on the outer surface of the shaft 34. The ball-shaped head 31 is connected by the neck 32 to the shaft 34 by means of a collar which has a load-supporting surface 33 on its underside. FIG. 3 may be considered as the front view of the femur portion of the endoprosthesis; the left-hand surface of the shaft may similarly be considered as the outside of the femur portion and the right-hand side as comprising the inside surface. In this view, the upper boundaries of the elongated indentations on the front of the shaft are indicated by numeral 40, there being only two of them provided in this case. In FIG. 4, these indentations are shown in profile and in both figures, the indentations attached to the rear side are indicated by numeral 41. If the line 42 in FIG. 3 and line 43 in FIG. 4 be considered as representing the longitudinal axis of the shaft of the femur portion, then FIG. 3 shows the mutual relationship of the orientation of the elongated indentations on the front and the rear of shaft 34. It is obvious that the indentations on the front of the shaft are disposed at angles which have an opposite sign with respect to the angles at which the indentations on the rear of the shaft are disposed.

As has already been mentioned, femur shafts shaped in accordance with the invention and implanted into the bones of sheep remained stable against rotation, whereas those without these indentations, even after long periods of implantation, have not been capable of achieving such a stability. It is believed that the rotation stability was caused by the firm growing onto and into the indentations 40 and 41 whereby the forces acting on the bone, which are perpendicularly oriented, remain insignificant in an oblique direction that the solidification effect on the tissue predominates.

We claim:

1. In a thigh portion of a cement-free implant of a hip joint total endoprosthesis, comprising a femur shaft, a head mounted on a neck attached to the upper end of the shaft, and a load supporting contact surface surrounding said neck, said implant having a biologically benign surface, said shaft being provided on its inner and outer sides with a series of outwardly projecting, transverse stepped, load-transferring flat surfaces, each of said surfaces being in a plane perpendicular to the longitudinal direction of orientation of the spicules of the spongy tissue in the femur adapted to be adjacent to each of said surfaces.

2. The invention defined in claim 1, wherein the contact surface surrounding the neck is disposed in a plane tilted with respect to the horizontal at an angle which is less than the normal angle of the neck of the thigh.

3. The invention defined in claim 1, wherein additional load-bearing, stepped surfaces are disposed at varying angles with respect to the horizontal.

4. The invention defined in claim 1, wherein said shaft is disposed asymmetrically with respect to the upper portions of the endoprosthesis when viewed from the direction lying to the outside of the shaft.

5. The invention defined in claim 1, wherein said shaft is also provided with indentations extending transversely across the respective opposite sides connecting the inner and outer sides.

6. In a femur portion of a cement-free, total implant endoprosthesis for a hip joint, comprising an elongated femur shaft having two opposite surfaces, each of said surfaces being provided with a series of transversely, vertically-spaced indentations, the upper boundaries of said indentations being disposed at an acute angle with respect to the axis of the shaft, the angular displacement of the upper boundaries of one side being opposite to the angular displacement of the upper boundaries on the opposite side.

7. The invention defined in claim 6, wherein said surface is provided with indentations constituting the front and rear sides of the shaft.

8. The invention defined in claim 6, wherein said shaft comprises a metal, the surface thereof being coated with a glasslike ceramic.

9. The invention defined in claim 8, wherein the composition of said implant comprises a dense ceramic containing more than 96% $Al_2O_3$.

10. The invention defined in claim 9, wherein the surface of said shaft is provided with a bio-active substance.

11. The invention defined in claim 6, wherein the inner and outer surfaces of the shaft are provided with a plurality of load-transferring, spaced steps.

12. The invention defined in claim 11, wherein said steps are disposed perpendicularly to the longitudinal orientation of the spicules of the spongy material surrounding the implant.

13. The invention defined in claim 11, wherein said shaft comprises a metal, the surface thereof being coated with a glasslike ceramic.

14. The invention defined in claim 11, wherein said implant comprises a dense ceramic containing more than 96% $Al_2O_3$.

15. The invention defined in claim 14, wherein the surface of said shaft is provided with a bio-active substance.

* * * * *